United States Patent
Schmidt (10) Patent No.: US 9,226,684 B2
(45) Date of Patent: Jan. 5, 2016

(54) METHOD FOR RECORDING MAGNETIC RESONANCE IMAGE DATA WHEN USING A VENTILATION APPARATUS

(71) Applicant: Sebastian Schmidt, Weisendorf (DE)

(72) Inventor: Sebastian Schmidt, Weisendorf (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 578 days.

(21) Appl. No.: 13/658,940

(22) Filed: Oct. 24, 2012

(65) Prior Publication Data

US 2013/0106414 A1   May 2, 2013

(30) Foreign Application Priority Data

Oct. 28, 2011  (DE) .......................... 10 2011 085 399

(51) Int. Cl.
*A61B 5/055* (2006.01)
*A61B 5/00* (2006.01)
*A61B 5/113* (2006.01)
*G01R 33/565* (2006.01)
*A61B 5/08* (2006.01)
*A61M 16/00* (2006.01)

(52) U.S. Cl.
CPC ................ *A61B 5/055* (2013.01); *A61B 5/113* (2013.01); *A61B 5/7292* (2013.01); *G01R 33/56509* (2013.01); *A61B 5/08* (2013.01); *A61M 16/00* (2013.01)

(58) Field of Classification Search
CPC ...................................... A61B 5/055
USPC ........................................ 324/309
See application file for complete search history.

(56) References Cited

U.S. PATENT DOCUMENTS

| | | | | |
|---|---|---|---|---|
| 4,712,560 A | * | 12/1987 | Schaefer et al. | 600/413 |
| 4,715,383 A | * | 12/1987 | Ehman et al. | 600/410 |
| 4,905,699 A | * | 3/1990 | Sano et al. | 600/413 |
| 5,691,641 A | * | 11/1997 | Cansell et al. | 324/309 |

(Continued)

FOREIGN PATENT DOCUMENTS

| | | |
|---|---|---|
| DE | 102005010093 A1 | 9/2006 |
| DE | 102008030891 A1 | 12/2009 |

(Continued)

OTHER PUBLICATIONS

L.W. Hendlund et al., "MR-compatible ventilator for small animals: computer-controlled ventilation for proton and noble gase imaging" in Magnetic Resonance Imaging 18 (2000), 754-759.*

(Continued)

*Primary Examiner* — Rodney Fuller (57) ABSTRACT

A method for recording magnetic resonance image data of a patient ventilated by means of a ventilation apparatus is provided. The method includes assigning influencing information describing the effect of a respiratory movement on the image data recording to pulse sequence information, determining a magnetic resonance protocol for actuating a magnetic resonance device and a ventilation protocol for actuating the ventilation apparatus, and coordinating with one another in time, taking into account the pulse sequence information together with the influencing information, an imaging objective and a ventilation requirement, and actuating the magnetic resonance device and the ventilation apparatus in a time-coordinated manner on the basis of the magnetic resonance protocol and the ventilation protocol.

16 Claims, 3 Drawing Sheets

(56) References Cited

U.S. PATENT DOCUMENTS

| | | | |
|---|---|---|---|
| 6,370,419 B1 | 4/2002 | Lampotang | |
| 7,257,436 B2 | 8/2007 | Sasaki | |
| 2004/0030235 A1* | 2/2004 | Sasaki et al. | 600/413 |
| 2004/0102695 A1* | 5/2004 | Stergiopoulos et al. | 600/413 |
| 2004/0155653 A1* | 8/2004 | Larson et al. | 324/309 |
| 2004/0230113 A1* | 11/2004 | Bolam et al. | 600/410 |
| 2005/0119560 A1* | 6/2005 | Mostafavi | 600/425 |
| 2005/0187464 A1* | 8/2005 | Ho et al. | 600/428 |
| 2006/0074300 A1* | 4/2006 | Green | 600/427 |
| 2008/0226149 A1* | 9/2008 | Wischmann et al. | 382/131 |
| 2009/0018433 A1* | 1/2009 | Kassai et al. | 600/413 |
| 2010/0127702 A1* | 5/2010 | Greiser et al. | 324/309 |
| 2010/0264925 A1* | 10/2010 | Stemmer | 324/309 |
| 2011/0152668 A1* | 6/2011 | Stemmer | 600/413 |
| 2011/0152669 A1* | 6/2011 | Kassai | 600/413 |
| 2012/0078083 A1* | 3/2012 | McConnell et al. | 600/413 |
| 2012/0271155 A1* | 10/2012 | Stemmer | 600/413 |
| 2013/0085375 A1* | 4/2013 | Hamill et al. | 600/413 |
| 2013/0134976 A1* | 5/2013 | Sugiura | 324/314 |
| 2013/0187649 A1* | 7/2013 | Bhat et al. | 324/307 |
| 2013/0225978 A1* | 8/2013 | Remmele et al. | 600/420 |
| 2013/0266200 A1* | 10/2013 | Miyazaki et al. | 382/131 |
| 2013/0281827 A1* | 10/2013 | Stemmer | 600/411 |

FOREIGN PATENT DOCUMENTS

| | | |
|---|---|---|
| DE | 102008032827 A1 | 1/2010 |
| DE | 102008049709 A1 | 4/2010 |
| EP | 1322972 B1 | 6/2010 |
| WO | WO2012028997 * | 3/2012 |

OTHER PUBLICATIONS

Chen Ben T., Yordanov Alexander .T., and Johnson G. Allan: Ventilation—Synchronous Magnetic Resonance Microscopy of Pulmonary Structure and Ventilation in Medicine, 2005, 53, S. 69-75.—ISSN 1522-2594; Others.

* cited by examiner

METHOD FOR RECORDING MAGNETIC RESONANCE IMAGE DATA WHEN USING A VENTILATION APPARATUS

CROSS REFERENCE TO RELATED APPLICATIONS

This application claims priority of German application No. 10 2011085399.5 DE filed Oct. 28, 2011. All of the applications are incorporated by reference herein in their entirety.

FIELD OF INVENTION

A method for recording magnetic resonance image data of a patient ventilated by means of a ventilation apparatus is provided. In addition an examination system comprising a magnetic resonance device and a ventilation apparatus is provided.

BACKGROUND OF INVENTION

Magnetic resonance tomography is a well-known and long-established imaging technology which is mainly employed in the medical imaging field. In most cases recording magnetic resonance image data takes a relatively long time, since for example a plurality of layers must be recorded one after another, and the like. Moreover, movements during the recording of an image lead to undesirable artifacts which have a detrimental effect on the image quality. Apart from other movements this applies in particular in the case of respiratory movements. For this reason magnetic resonance devices are known which at certain time instants during the recording of the image data output what are known as breath-hold commands so that a patient who is the subject of a magnetic resonance image data acquisition can hold his or her breath for a certain period of time and as a result motion artifacts can be avoided. In the magnetic resonance tomography of ventilated patients there is however the problem that said conventional breath-hold commands, which are issued automatically by the magnetic resonance device, do not work correctly. It has therefore been proposed that a ventilation apparatus will be briefly stopped manually during the recording of magnetic resonance image data whenever the operator of the magnetic resonance device issues a corresponding command to an anesthetist actuating the ventilation apparatus. This process is complicated and prone to error and optimal results cannot be obtained.

With regard to other imaging techniques, solutions have already been discussed which are aimed at improving the image quality in the event of a respiratory movement or indeed to avoid respiratory movement artifacts. Thus, it is provided in DE 10 2008 032 827 A1 to take into account in the reconstruction of the image data a ventilation signal of a ventilation device used in any case for ventilating a patient under general anesthetic who is being examined by means of a medical imaging system, so that no separate device for measuring the respiratory movement is required. For example, the ventilation signal can be used for gating in respect of the respiration. In DE 10 2008 030 891 A1 it is proposed to interrupt the ventilation of an anesthetized patient by means of a ventilation device as a function of a sensed operating status of a medical system fully automatically for the duration of a diagnostic or therapeutic examination. The intention in doing this is to relieve the pressure on the medical personnel.

A common feature of the two cited possibilities is that they are very poorly suited to use in connection with magnetic resonance tomography, which is due in particular to the duration of the recording of the magnetic resonance image data. Thus, there is no question of the ventilation device (ventilation apparatus) being stopped for the entire duration of the image recording session. The condition of many patients who are to undergo examination is poor, so that only very brief ventilation pauses, if any, are conceivable. The long duration of the pulse sequences in magnetic resonance also conflicts with the idea of controlling the start of the magnetic resonance acquisition as a function of the ventilation cycle, because a certain time elapses until magnetic resonance image data is actually measured and the respiratory position changes. Consequently, techniques such as those cited above, which are designed for x-ray-based imaging methods, are only usable to a very limited extent within the framework of magnetic resonance.

SUMMARY OF INVENTION

An object is therefore to disclose a control method by means of which magnetic resonance image data of improved quality in respect of the respiratory movement in the case of ventilated patients can be recorded without putting the patient at risk.

In order to achieve this object it is inventively provided in the case of a method of the type cited in the introduction that
  use is made of pulse sequence information to which influencing information describing the effect of a respiratory movement on the image data recording is assigned,
  a magnetic resonance protocol for actuating a magnetic resonance device and a ventilation protocol for actuating the ventilation apparatus are determined, coordinated with one another in time, while taking account of the pulse sequence information together with the influencing information, an imaging objective and a ventilation requirement, and
  the magnetic resonance device and the ventilation apparatus are actuated in a time-coordinated manner on the basis of the magnetic resonance protocol and the ventilation protocol.

It is therefore proposed that the magnetic resonance protocol and the ventilation protocol are produced and executed coordinated with one another in such a way that the negative influencing of the magnetic resonance image data by the ventilation is minimized and at the same time—described by the ventilation requirement—no risk to the ventilated patient arises. In particular it can be provided for this purpose that the magnetic resonance device and the ventilation apparatus are coupled to one another by way of an interface, for example a CAN bus, such that both devices can exchange information. In this case the performance of the method relates to the thus coupled examination system, it being ultimately immaterial where calculations are carried out or inputs received.

Within the scope of an embodiment, contrary to practice in the prior art, the ventilation device is in this case not simply switched on/off, but instead the ventilation cycles are coordinated with the pulse sequences of the magnetic resonance protocol such that the respiratory movement exerts no influence or a minimum possible influence. For example, as will be dealt with in more detail herein below, the ventilation cycles can therefore be staggered with the cycles of the pulse sequences such that the minimum possible influencing is present or the ventilation cycles can be chosen such that the movements of the lung take place during the pauses in the pulse sequence, in which no data is measured, for example in TE intervals in the case of spin-echo sequences.

An automatic optimization, in particular performed by at least one control device, of the interaction of magnetic resonance device (or pulse sequence/protocol) and ventilation apparatus, i.e. the ventilation protocol (ventilation scheme), therefore takes place, wherein one of the protocols or both protocols is or are modified on the basis of the other in each case. This results in optimal image quality in the case of ventilated patients.

As has already been explained, the ventilation apparatus is not simply deactivated, such that in particular at least one ventilation cycle, in particular a plurality of ventilation cycles, take(s) place over the entire duration of the image data recording.

At the same time various possibilities exist with regard to the actual approach adopted. Thus, for example, it can be provided that a ventilation protocol is calculated starting from the basis of a magnetic resonance protocol selected in accordance with the imaging objective. Thus, for example, a magnetic resonance protocol corresponding to the imaging objective, for example a recording of a specific target region, can be selected on a magnetic resonance device. In addition to the pulse sequence information, said magnetic resonance protocol also contains influencing information, for example information relating to the sections of the pulse sequences in which respiratory movements have no detrimental effect on the image quality, or information relating to which type of respiratory movements are possible in the respective phases of the protocol, which can be described for example on the basis of at least one influencing variable. A corresponding ventilation protocol is calculated on the basis of this information. Said ventilation protocol is checked to determine whether it is suitable for the patient, in other words the ventilation requirement is therefore fulfilled. It can be checked for example whether the necessary air supply in liters/minute is achieved. If no ventilation protocol meeting the ventilation requirement can be found, it can be provided that an adjustment of the magnetic resonance protocol takes place. Thus, if no suitable corresponding ventilation protocol can be found, the magnetic resonance protocol can be modified for example in that other pulse sequences fulfilling the imaging objective are chosen, and the like.

A magnetic resonance protocol and a ventilation protocol determined in this way are then, as already described in general terms, executed in parallel, i.e. the control information contained in them is used for actuating the devices, with a correlation in time continuing to exist.

However, it is obviously also conceivable to calculate a magnetic resonance protocol starting from the basis of a ventilation protocol meeting the ventilation requirements. In this embodiment the ventilation scheme or ventilation protocol is therefore set on the ventilation apparatus. From this, a movement scheme for example can now be calculated and the magnetic resonance measurements are automatically arranged such that they take place at a time with minimum possible movement. In this case a similar approach as in the just described case can ultimately be adopted so that for example even if the imaging objective is not achieved, another ventilation protocol fulfilling the ventilation requirement is chosen as starting point, or the like.

An influencing variable can be used to describe the effect of respiratory movements on the image data recording. Such a variable can for example specify how greatly the magnetic resonance image data recorded with a respiratory movement deviates from magnetic resonance image data recorded in a recording region without movement. Such influencing variables can be determined by means of experiments on phantoms or patients, or it is possible to determine them by means of model calculations. For example, a movement sensitivity can be defined as a value from 0 to 100%. It is advantageous in particular in this connection if an influencing variable reproduced in a time-resolved manner over the duration of the corresponding pulse sequence is specified as part of the influencing information. In this way it can be assessed in which time segments of a pulse sequence a strong influence is present and in which time segments a less strong influence is present, wherein respiratory movements in the regions of weaker influence can be provided within the scope of the coordination, and the like.

Numerous other possibilities of specifying influencing information are, of course, also conceivable. Influencing information can also directly contain information relating to how much ventilation air can be introduced into the patient during a single k-space filling and/or how strong a lack of definition of the diaphragms in the image space may be during a pulse sequence. It is however preferred to perform observations in the k-space, since full passes through the k-space in particular must be performed as consistently as possible.

Influencing information can preferably be determined from measured data of at least one test measurement. It should be pointed out in particular in this regard that ventilation protocols between differently implemented ventilation devices can in most cases be compared adequately well with one another. In particular it is mostly the case as part of the setting of the ventilation apparatus to specify a total ventilation volume, i.e. an amount of respiratory air which is to be inhaled during a ventilation cycle, and a flow rate which specifies how fast the respiratory air is administered to the patient. Starting from such parameters, a user, in particular a physician, expects a specific effect, for which reason available ventilation devices can be compared and consequently test measurements are useful in order to furnish the pulse sequence information with the influencing information, in particular already on the manufacturer side.

Beneficially, it can therefore be provided that the influencing information includes information relating to pulse sequence segments in which a respiratory movement has no effect on the image data quality and/or information about which respiratory movements are possible during a pulse sequence segment if a threshold value for an influencing variable is undershot. In this way it is possible to assign movement processes resulting due to the ventilation by means of the ventilation apparatus to corresponding phases of the at least one pulse sequence of the magnetic resonance protocol.

Thus, it can be provided for example that the magnetic resonance protocol and the ventilation protocol are calculated in such a way that a ventilation takes place in recording pauses and/or that during a recording period a respiratory movement is present which undershoots a threshold value for an influencing variable and/or which generates an error which can be at least partially compensated for computationally given knowledge of the present respiratory movement. While it is therefore entirely conceivable to arrange the ventilation cycles such that they take place in the recording pauses, i.e. consequently a kind of staggered arrangement of ventilation cycles and pulse sequences or recording cycles is given, it is furthermore also conceivable to accept a certain imprecision or to accept a thus defined, slight movement such that it can be computationally compensated for or made use of.

In a further embodiment, it can be provided that within the scope of the adjustment of the magnetic resonance protocol at least one layer that is to be measured in the patient is chosen such that it can be measured during a respiratory movement specified by the ventilation protocol undershooting a threshold value for an influencing variable, in particular the entire layer arrangement and/or layer measurement sequence is chosen such that it can be measured coordinated with the respiratory movements specified by the ventilation protocol undershooting a threshold value for an influencing variable. It frequently happens that some layers that are to be recorded are affected differently, in particular less, by respiratory movements than other layers. It is the case for example that the upper portions of the thorax exhibit less movement during breathing, while a stronger influence due to the respiratory movement is present in the abdominal region or in the lower thorax. In contrast, lower abdomen organs in turn move more weakly than upper abdomen organs. This knowledge can now be used in order for example to measure more strongly moving regions of the human body in the ventilation pauses, while in the movement phases regions of the human body are measured which in any case exhibit only an extremely weak or at least weaker respiratory movement. For example, the regions or the pulse sequences matched to the respective layer can be assigned an influencing variable which permits the corresponding arrangement or assignment of layers to be recorded to ventilation cycles (or their phases) or ventilation pauses.

It can furthermore be provided that within the scope of the adjustment of the magnetic resonance protocol at least one pulse sequence and/or one pulse sequence segment is chosen such that a time period characterizing the variation with time of the image data recording and/or the duration of recording pauses, in particular an echo time, is adjusted, in particular extended. The magnetic resonance protocol can therefore be determined in a targeted manner such that time periods time periods and pulse sequences are adjusted in order for example to "accommodate" ventilation cycles and the like. In the case of turbo spin-echo sequences (TSE sequences), for example, the lengths of the echo cycles can be varied. Toward that end it can for example first be calculated or communicated by the ventilation apparatus which ventilation pauses are possible at a maximum so that subsequently an echo train length which can be selected during such a ventilation pause is chosen automatically.

It can furthermore be provided that within the scope of an adjustment of the ventilation protocol the execution of at least one ventilation cycle is modified, in particular in terms of the duration of the ventilation cycle and/or of the time sequence of the respiratory movement. In concrete terms it can be provided for example that a high-frequency ventilation is performed at least temporarily. A very high ventilation rate, for example over 150 ventilation cycles per minute, can be achieved by means of a high-frequency ventilation. There are various types of high-frequency ventilation, for example what is known as "high-frequency jet ventilation" and "high-frequency oscillatory ventilation". Such high-frequency ventilation techniques therefore enable shorter timespans to be used for a complete ventilation cycle, which is extremely advantageous. It can in particular also be provided in this case that the ventilation method is changed over during the recording, with for example conventional ventilation being used in recording pauses and a high-frequency ventilation, for example a "high-frequency jet ventilation", being used during a pulse sequence in time periods of low influence.

It is, however, also possible within the scope of the adjustment of the execution of ventilation cycles that the time sequence of the respiratory movement is adjusted. With certain recording techniques, such an adjustment can be accompanied by great benefits, reference being made only by way of example to the method described in DE 10 2005 010 093 A1 for displaying respiration patterns. It is proposed therein to separate signal components of the blood from signal components of a lung parenchyma in such a way that magnetic resonance images of the lung are recorded in the variation with time with a very short recording duration, whereby the variation of the signal with time is determined in the magnetic resonance images. The Fourier transform of the variation of the signal with time is formed so that the Fourier spectrum associated with the lung parenchyma can be extracted and the corresponding information can be displayed in the magnetic resonance image. Fast spin-echo sequences can be used, for example, in which the recording of a magnetic resonance image in the range of 0.1-0.5 seconds, preferably 0.3 seconds, is possible. Gradient echo sequences can also be used if low field strengths are present. With such an imaging objective or the use of such magnetic resonance protocols, the ventilation curve can for example be chosen with the greatest possible similarity to a sine curve, such that the peak in the spectrum following the Fourier transform is extremely narrow and consequently the spectral resolution is particularly easily possible. In this connection a plurality of magnetic resonance images are of course recorded in a targeted manner during the ventilation.

It can furthermore be provided that the magnetic resonance protocol and the ventilation protocol are determined in such a way that the same phase of the respiratory movement is always present at a specific time instant of a pulse sequence. The ventilation cycles and the at least one pulse sequence can therefore also be synchronized such that in each case at a specific time instant of the pulse sequence (or at multiple specific time instants of the pulse sequence) a specific position of the examined target region or organ is present. If, therefore, the layer selection gradient, for example, is always applied during the inspiration, in which event the liver, for example, is located 5 cm deeper than during the expiration, this displacement, since it is present as part of the targeted region and is known, can automatically be compensated for.

In a further embodiment, it can be provided that during the execution of the protocols a measurement of at least one ventilation parameter characterizing the ventilation quality can be taken continuously and/or cyclically, an adjustment of the magnetic resonance protocol and/or of the ventilation protocol being carried out or the execution of the protocols being aborted if the ventilation parameter exceeds or falls below a threshold value. It can therefore also be provided to monitor the condition of the patient constantly in order thereby to increase the overall safety of the process. Thus, ventilation parameters are continuously determined, as a function of which the current strategy described by the protocols is modified automatically, or indeed the recording of the magnetic resonance image data is aborted completely. In order to modify the protocols it can for example be provided that the echo train of a turbo spin-echo sequence (TSE sequence) is automatically shortened in order to allow more ventilation cycles per unit time. For example, it can be provided that a composition of the exhaled gases and/or an oxygen saturation of the blood are/is measured. Measurement instruments for measuring such ventilation parameters are widely known in the prior art and shall not be explained in greater detail here.

In another beneficial embodiment, it can be provided that the magnetic resonance protocol is determined in such a way that during a specific ventilation cycle, in particular during the first ventilation cycle, magnetic resonance image data is recorded from which compensation information for compensating for motion effects in further magnetic resonance image data and/or a phase correction factor describing the time offset between an actuation of the ventilation apparatus and the associated respiratory movement of the patient are/is derived. Thus, for example, magnetic resonance image data recorded in the first ventilation cycle can be used for optimizing the pulse sequence or for compensation purposes. It is conceivable, for example, to determine the change in position of the liver once as a function of the inspiration volume and subsequently proceed on the assumption that the same behavior will be repeated in all further ventilation cycles.

Here, too, it is furthermore conceivable that an adjustment of the magnetic resonance protocol and/or of the ventilation protocol is made as it were "online" as a function of magnetic resonance image data already recorded within the scope of the magnetic resonance protocol. Particularly advantageously, a phase correction is determined which reflects the time offset between the activity of the ventilation apparatus and the respiratory movement actually taking place. The volume of the hoses, more generally the dead volume of the ventilation apparatus, can be compensated for in this way. This is particularly important within the framework of magnetic resonance imaging, because when the magnetic resonance image data is being recorded the ventilation device is arranged further away from the patient than is usually the case.

It can particularly advantageously be provided that when the protocols are determined and/or the magnetic resonance image data is evaluated at least one phase correction factor is taken into account which describes the time offset between an actuation of the ventilation apparatus and the associated respiratory movement of the patient. As already mentioned, such a phase correction factor can be determined by measurements, although it also possible to determine said factor computationally, for example if the dead volume present in the ventilation apparatus is known, and the like.

As already explained, it can beneficially be provided that the magnetic resonance device, more particularly a control device of the magnetic resonance device, and the ventilation apparatus, more particularly a control device of the ventilation apparatus, communicate with one another via a communications link, preferably a bus, in particular a CAN bus. A bus system, in particular a CAN bus, forms a particularly suitable interface for combining a magnetic resonance device and a ventilation apparatus into a common examination system, while obviously further peripheral devices of a magnetic resonance device can also be connected via a CAN bus and can then communicate with one another for the purpose of controlling the overall system.

In addition to the method, an examination system, comprising a magnetic resonance device having a control device, a ventilation apparatus having a control device, and a communications link, in particular a bus, between the control devices, the control device of the magnetic resonance device and/or the control device of the ventilation apparatus being embodied for performing the method. All embodiments in relation to the method can be applied analogously to the examination system, by means of which it therefore follows that the same advantages can be obtained.

It is particularly preferred in this case if the control device of the magnetic resonance device is embodied for performing the method, since then the influencing information assigned to the pulse sequence information can already be stored in the magnetic resonance device itself, which influencing information, as explained, can essentially be determined so as to be valid also for different ventilation devices. The ventilation apparatus can then be attached to the magnetic resonance device by way of a corresponding connection or via a corresponding interface, such that a communications link is established and information can be exchanged, in particular in relation to the ventilation requirement and/or the ventilation protocol, so that for example the most recently determined ventilation protocol can be transmitted to the control device of the ventilation apparatus, and the like.

Typically, both the ventilation apparatus and the magnetic resonance device also have an operator device at which inputs can be made and information can be displayed. A ventilation requirement or a proposal for one of the protocols can accordingly be input by way of such an operator device, whereupon magnetic resonance protocol and ventilation protocol are then coordinated automatically by means of the control device or control devices.

BRIEF DESCRIPTION OF THE DRAWINGS

Further advantages and details will emerge from the exemplary embodiments described hereinbelow as well as with reference to the drawing, in which.

DETAILED DESCRIPTION OF INVENTION

Figure 1:
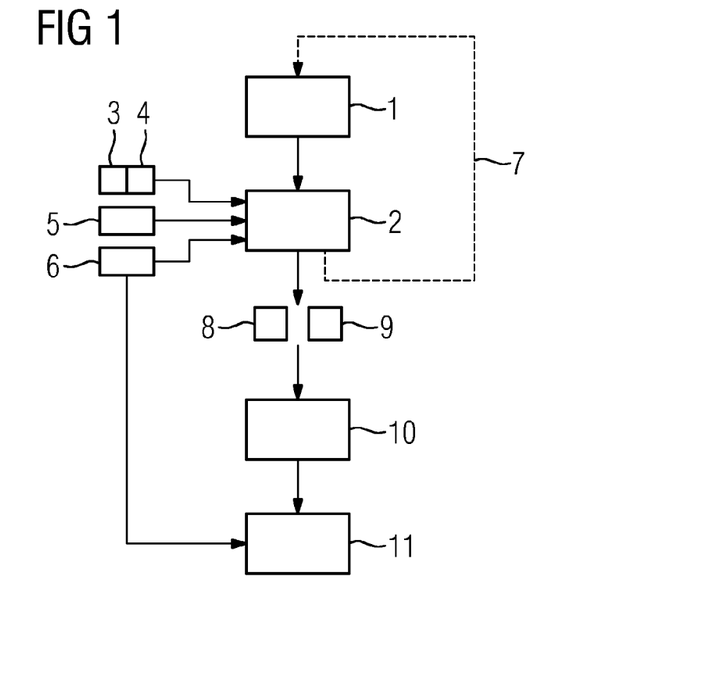
FIG. 1 shows a basic flowchart of an exemplary embodiment of the method.

FIG. 1 shows a basic flowchart of an exemplary embodiment of the method. What is concerned here is the control of the recording mode of operation for acquiring magnetic resonance image data in the case of a patient receiving respiratory assistance by means of a ventilation apparatus, wherein control protocols which are required to be executed in parallel are determined for the magnetic resonance device and the ventilation apparatus and used, in which control protocols the effect on the image quality due to the ventilation is minimized and nonetheless the ventilation requirement for the patient is fulfilled.

In the case of the present exemplary embodiment, a magnetic resonance protocol matched to the imaging objective, for example a recording of the patient's thorax, is initially selected in step 1. This can happen automatically on the basis of data available to the magnetic resonance device, though it is also conceivable for a user to select his or her preferred protocol.

In a step 2, starting from the basis of said magnetic resonance protocol, a ventilation protocol for controlling the ventilation apparatus is then determined automatically. In this case different information is taken into consideration, in particular in the first instance pulse sequence information 3, to which influencing information 4 describing the effect of a respiratory movement on the image data recording is assigned. The influencing information 4, which advantageously has been determined by measurement, for example as influencing variables, is stored together with the pulse sequence information in the magnetic resonance device. In the present case it comprises information relating to pulse sequence segments in which a respiratory movement has no effect on the image data quality, and information relating to which respiratory movements are possible during a pulse sequence segment if a threshold value for an influencing variable is undershot.

Also taken into account is an imaging objective 5 which reflects for example which target region inside the patient is to be recorded and what type of information is to be determined from said target region, for example whether a functional magnetic resonance imaging session is to take place, and the like. Such an imaging objective is made available to the magnetic resonance device usually as a result of a corresponding input by a user and/or from a patient registration, for example also transmitted with the aid of an information system. Lastly, a ventilation requirement for the patient is taken into account which for example can be input by way of the ventilation apparatus and/or be stored there. The ventilation requirement can for example specify how many liters of air per minute are to be supplied as a minimum to the patient, and the like.

If it is not possible to determine a ventilation protocol such that the ventilation requirement 6 is fulfilled, the magnetic resonance protocol is adjusted or a completely new magnetic resonance protocol is chosen; cf. also arrow 7.

If, however, a magnetic resonance protocol 8 and a ventilation protocol 9 coordinated with one another were determined in step 2, these are used in a step 10 to actuate the magnetic resonance device and the ventilation apparatus respectively, while taking the time coordination between the protocols 8, 9 into account.

In addition to the exemplary embodiment shown in FIG. 1 it is of course possible also to specify a ventilation protocol 9 which fulfills the ventilation requirements 6, and to determine a magnetic resonance protocol 8 coordinated therewith. An alternating coordination of protocols 8, 9 with one another is also conceivable.

Numerous possibilities exist for coordinating the protocols 8, 9 with one another in step 2, so that for example the protocols 8, 9 can be determined such that a ventilation is performed in recording pauses, that a respiratory movement undershooting a threshold value for an influencing variable is present during a recording period, that a respiratory movement is present which generates an error which can be at least partially compensated for computationally given knowledge of the present respiratory movement, that the sequence of layers to be measured or the arrangement of layers to be measured is adjusted, that pulse sequences or pulse sequence segments are selected such that specific time periods are adjusted to ventilation cycles, that a ventilation cycle itself is adjusted, for example in terms of the duration or of the time sequence, and the like. In particular, high-frequency ventilation techniques can also be employed.

Concrete exemplary embodiments or coordination possibilities will be explained in more detail below also with reference to FIGS. 2-5. Firstly, however, referring further to FIG. 1, ventilation parameters describing the ventilation quality are measured continuously in a step 11 during the execution of the protocols 8, 9. For example, a composition of the exhaled gases and/or an oxygen saturation of the blood can be measured. Said ventilation parameters or parameters derivable therefrom are compared with a threshold value which can be associated with the ventilation requirement 6, in particular can be derived from the latter. If said threshold value is exceeded or, as the case may be, undershot, depending on the type of the ventilation parameter, a risk exists for the patient, for which reason two possibilities are provided. While it is possible on the one hand to abort the image data recording, it is preferred to adjust the magnetic resonance protocol and/or the ventilation protocol so that the threshold value and in particular also the ventilation requirement 6 are fulfilled. A dynamic adjustment of the protocols 8, 9, which can also be based on other criteria, is therefore conceivable.

Thus, it is namely also possible for example to use the magnetic resonance protocol 8 and the ventilation protocol 9 to record first magnetic resonance image data which serves solely for the evaluation with regard to parameters required in the further course of recording, which parameters may, where appropriate, also lead to a further adjustment of the magnetic resonance protocol 8 and/or of the ventilation protocol 9. Thus, it is conceivable on the one hand to measure the target region, in particular during an entire ventilation cycle, in order to obtain compensation information to compensate for motion effects in further magnetic resonance image data. Thus, for example, the movement of an organ that is to be recorded can be traced during the inspiration and the expiration so that these time instants are known. If, for example, the magnetic resonance image data is recorded in accordance with the mutually coordinated protocols 8, 9 in such a way that a specific movement status in terms of the respiratory movement is always present at specific time instants of a pulse sequence, i.e. consequently that a specific phase of the respiratory movement is given, then corresponding compensation parameters can be measured within the protocols 8, 9 themselves. The compensation information can be taken into consideration within the scope of the evaluation.

With particular advantage it is, however, provided in the case of this exemplary embodiment that within the scope of the first ventilation cycle a phase correction factor describing the time offset between an actuation of the ventilation apparatus and the associated respiratory movement of the patient is determined, for which purpose magnetic resonance image data is evaluated. Such a time lag is given as a result of the dead volume in components of the ventilation apparatus, which is arranged further away from the patient during magnetic resonance imaging than in the case of other imaging techniques. Said phase correction factor, which alternatively can be determined also by calculation if the characteristics of the ventilation apparatus are known, can be taken into account in any further adjustment of the protocols 8, 9 that may be necessary.

However, such a phase correction factor can of course be taken into account also within the scope of the evaluation of the magnetic resonance image data, in particular when compensation information is also present which is directed at specific movement phases at specific time instants of a pulse sequence, for the respiratory movement can take place with an offset relative to the actuation of the ventilation protocol 9.

Concrete examples of the coordination of the protocols 8, 9 are now to be explained in more detail with reference to FIGS. 2-5.

Figure 2:
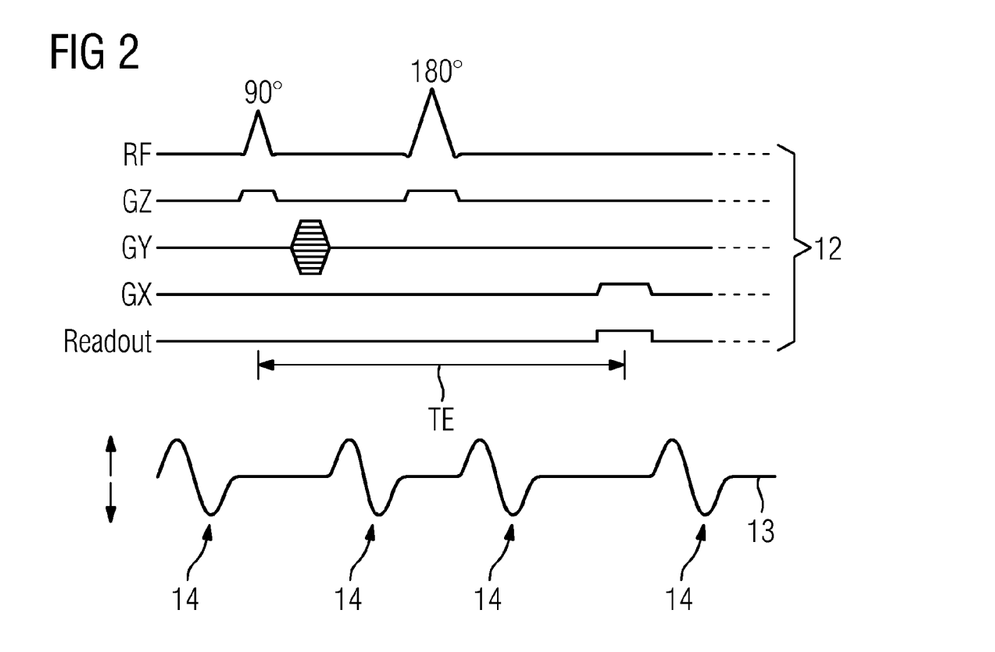
FIG. 2 shows a spin-echo pulse sequence and an associated determined sequence of ventilation cycles.

FIG. 2 shows, in the top part of the diagram, a spin-echo pulse sequence 12, wherein the waveforms of the high-frequency signal (RF), the gradient pulses (GX, GY, GZ) and the readout gradient (Readout) are plotted. The echo time is designated by TE.

The graph 13 corresponding in time shows the sequence of ventilation cycles 14, which is coordinated with the pulse sequence 12. The influencing information 4 in this case contains the phases or time sections of the pulse sequence 12 in which no pulses are present, i.e. no gradient pulses and no high-frequency pulses, in other words in which recording pauses exist. The movement cycles 14 are chosen here such that they lie within said recording pauses. A staggered arrangement of pulses and ventilation cycles is therefore established.

It should also be pointed out at this juncture that the spin-echo pulse sequence 12 can also be modified such that for example a longer echo time TE is provided if the previous spin-echo time TE failed to allow for adequate recording pauses, and the like.

Figure 3:
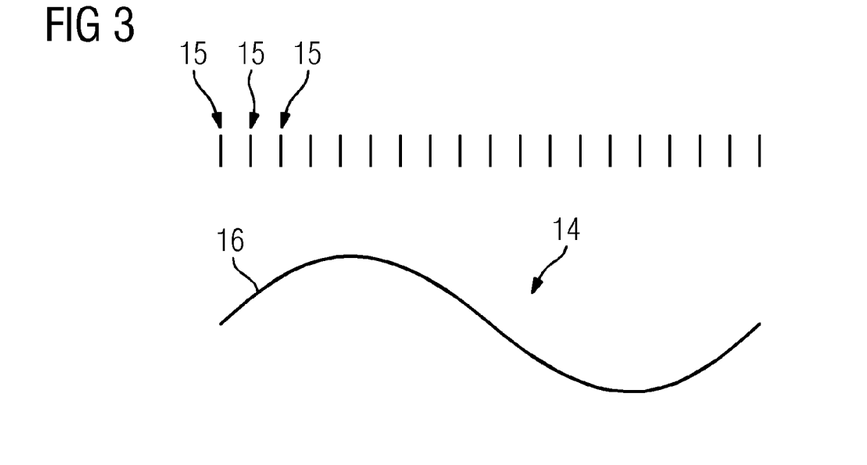
FIG. 3 shows a schematic representation of a result of a method during the display of respiration patterns.

FIG. 3 illustrates a further example in which a method according to DE 10 2005 010 093 A1 for displaying respiration patterns, in particular in order to analyze a lung parenchyma, is performed. In this case magnetic resonance images are recorded in very rapid succession, exemplary recording time instants 15 being shown in the top part of FIG. 3. In this exemplary embodiment the sequence 16 of the respiratory movement is now adjusted, in this case by the actuation receiving a sine curve 16 for one ventilation cycle 14 of the ventilation apparatus. This results in a relatively clearly defined peak in the Fourier transform, thereby favoring the spectral resolution.

Figure 4:
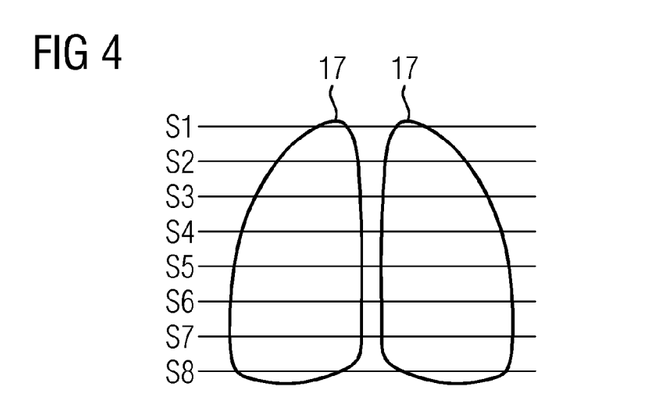
FIG. 4 shows different layers during the recording of a thorax.
Figure 5:
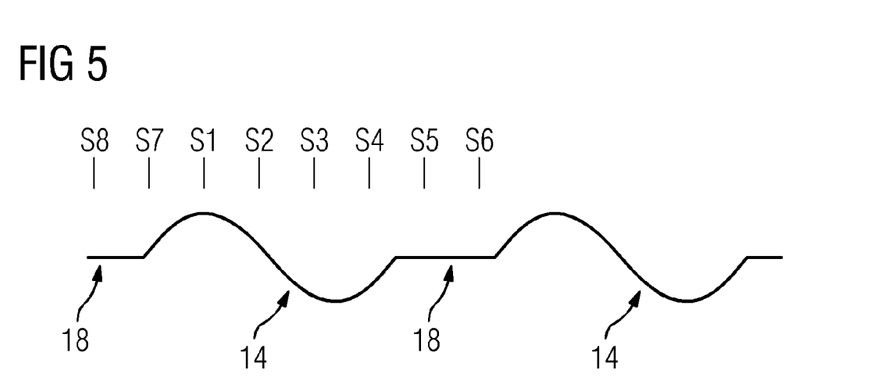
FIG. 5 shows the recording of the layers relative to ventilation cycles.

A further possibility for coordinating the protocols 8, 9 to one another is shown in FIGS. 4 and 5. According to FIG. 4, magnetic resonance image data is to be recorded in the region of the thorax, that is to say in particular of the lungs 17. The recording is performed in a plurality of layers S1-S8, which are indicated accordingly in FIG. 4. Now it is, however, well-known (and derivable from the influencing information 4) that the upper region of the thorax is much less affected by respiratory movements than the lower region of the thorax. The sequence in which the layers S1-S8 are measured is chosen here such that the lower portions of the thorax are measured in ventilation pauses 18 and the upper portions, which move less during respiration, in the movement phases. This is illustrated in greater detail by FIG. 5, in which two movement cycles 14 in the course of the ventilation are shown. As can be seen, the layers S8 and S7 are initially measured in a ventilation pause 18, this process being continued with the layers S1, S2, S3 and S4 during the respiratory movement. The layers S5 and S6 are then measured in turn in a ventilation pause 18. Obviously numerous other embodiments are also conceivable which permit a coordination of the magnetic resonance protocol 8 and the ventilation protocol 9.

Figure 6:
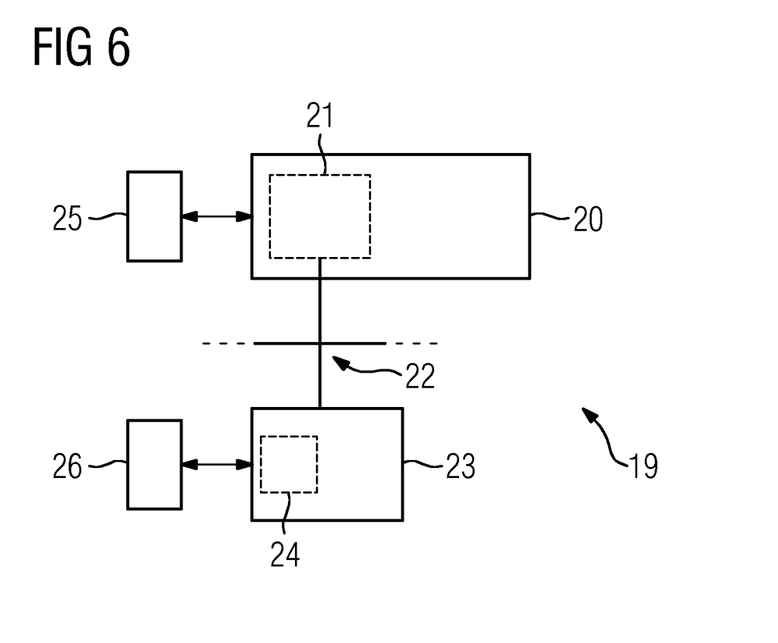
FIG. 6 shows an examination system.

Finally, FIG. 6 shows a schematic layout of an examination system 19 which comprises a magnetic resonance device 20, as is known in more detail from the prior art and does not need to be explained further here, having a control device 21. This is connected to a CAN bus 22, which represents the interface to a ventilation apparatus 23 which is likewise connected to the CAN bus 22 and also has a control device 24. A communications link is therefore established by way of the CAN bus 22.

The control devices 21 and 24 are able to control the magnetic resonance device 20 and the ventilation apparatus 23 as a function of a magnetic resonance protocol 8 and a ventilation protocol 9, respectively. In the case of this exemplary embodiment the control device 21 is embodied to perform the method, the corresponding information being provided in part by the control device 24. Obviously, however, embodiments are also conceivable in which the control device 24 performs the method according to the invention or, alternatively, the implementation of the method is divided among the control devices 21 and 24.

The magnetic resonance device 20 can be assigned an operator device 25 via which inputs can be made and information displayed. Equally, the ventilation apparatus 23 can also include an operator device 26.

Further communicating devices can, of course, also be connected to the CAN bus.

I claim:

1. A method for recording magnetic resonance image data of a patient ventilated by means of a ventilation apparatus, comprising:
    assigning influencing information describing an effect of a respiratory movement on quality of the magnetic resonance image data to pulse sequence information;
    determining a magnetic resonance protocol for actuating a magnetic resonance device and a ventilation protocol for actuating the ventilation apparatus and coordinating with one another in time taking into account the pulse sequence information together with the influencing information, an imaging objective and a ventilation requirement; and
    actuating the magnetic resonance device and the ventilation apparatus in a time-coordinated manner on the basis of the magnetic resonance protocol and the ventilation protocol,
    wherein the magnetic resonance device is actuated for recording the magnetic resonance image data in layers according to a sequence, and
    wherein the sequence of the layers is determined based on the effect of the respiratory movement on the quality of the magnetic resonance image data such that some of the layers are recorded during movement phases where the respiratory movement has less effect on the quality of the magnetic resonance image data and some of the layers are recorded during ventilation pauses where the respiratory movement has more effect on the quality of the magnetic resonance image data.

2. The method as claimed in claim 1, wherein the ventilation protocol is determined starting from the magnetic resonance protocol selected with regard to the imaging objective.

3. The method as claimed in claim 2, wherein the magnetic resonance protocol is adjusted when no ventilation protocol fulfilling the ventilation requirement is found.

4. The method as claimed in claim 1, wherein the magnetic resonance protocol is determined starting from a ventilation protocol fulfilling the ventilation requirement.

5. The method as claimed in claim 1, wherein the magnetic resonance protocol and the ventilation protocol are determined in such a way that a ventilation takes place in recording pauses and/or in that during a recording period a respiratory movement is present which undershoots a threshold value for an influencing variable and/or generates an error which is at least partially compensated for computationally given knowledge of the present respiratory movement.

6. The method as claimed in claim 1, wherein within the scope of the adjustment of the magnetic resonance protocol a pulse sequence and/or one pulse sequence segment is chosen such that a time period characterizing a variation with time of the image data recording and/or the duration of recording pauses is adjusted.

7. The method as claimed in claim 6, wherein the duration of an echo time is extended.

8. The method as claimed in claim 1, wherein within the scope of an adjustment of the ventilation protocol the execution of a ventilation cycle is adjusted.

9. The method as claimed in claim 8, wherein the duration of the ventilation cycle and/or the time sequence of the respiratory movement is adjusted.

10. The method as claimed in claim 8, wherein a high-frequency ventilation is performed at least temporarily.

11. The method as claimed in claim 1, wherein the magnetic resonance protocol and the ventilation protocol are determined in such a way that the same phase of the respiratory movement is always present at a specific time instant of a pulse sequence.

12. The method as claimed in claim 1,
    wherein during the execution of the magnetic resonance protocol and a ventilation protocol a measurement of a ventilation parameter characterizing the ventilation quality is taken continuously and/or cyclically, and wherein an adjustment of the magnetic resonance protocol and/or of the ventilation protocol is carried out or the execution of the magnetic resonance protocol and the ventilation protocol is aborted when the ventilation parameter exceeds or falls below a threshold value.

13. The method as claimed in claim 1, wherein the magnetic resonance protocol is determined in such a way that during a specific ventilation cycle, magnetic resonance image data is recorded from which compensation information for compensating for motion effects in further magnetic resonance image data and/or a phase correction factor describing the time offset between an actuation of the ventilation apparatus and the associated respiratory movement of the patient are/is derived.

14. The method as claimed in claim 13, wherein the specific ventilation cycle is the first ventilation cycle.

15. The method as claimed in claim 1, wherein when the magnetic resonance protocol and the ventilation protocol are determined and/or the magnetic resonance image data is evaluated a phase correction factor is taken into account which describes the time offset between an actuation of the ventilation apparatus and the associated respiratory movement of the patient.

16. An examination system, comprising:
a magnetic resonance device having a first control device;
a ventilation apparatus having a second control device; and
a communications link, between the first and second control devices, wherein the first control device and/or the second control device are embodied for performing a method, and wherein the method comprises:
assigning influencing information describing an effect of a respiratory movement on quality of the magnetic resonance image data to pulse sequence information;
determining a magnetic resonance protocol for actuating a magnetic resonance device and a ventilation protocol for actuating the ventilation apparatus and coordinating with one another in time taking into account the pulse sequence information together with the influencing information, an imaging objective and a ventilation requirement; and
actuating the magnetic resonance device and the ventilation apparatus in a time-coordinated manner on the basis of the magnetic resonance protocol and the ventilation protocol,
wherein the magnetic resonance device is actuated for recording the magnetic resonance image data in layers according to a sequence, and
wherein the sequence of the layers is determined based on the effect of the respiratory movement on the quality of the magnetic resonance image data such that some of the layers are recorded during movement phases where the respiratory movement has less effect on the quality of the magnetic resonance image data and some of the layers are recorded during ventilation pauses where the respiratory movement has more effect on the quality of the magnetic resonance image data.

* * * * *